(12) United States Patent
Vandervort

(10) Patent No.: US 10,164,952 B2
(45) Date of Patent: *Dec. 25, 2018

(54) METHOD AND SYSTEM FOR SERVER BASED SECURE AUDITING FOR REVISIONING OF ELECTRONIC DOCUMENT FILES

(71) Applicant: Xerox Corporation, Norwalk, CT (US)

(72) Inventor: David R. Vandervort, Walworth, NY (US)

(73) Assignee: Xerox Corporation, Norwalk, CT (US)

( * ) Notice: Subject to any disclaimer, the term of this patent is extended or adjusted under 35 U.S.C. 154(b) by 330 days.

This patent is subject to a terminal disclaimer.

(21) Appl. No.: 15/044,607

(22) Filed: Feb. 16, 2016

(65) Prior Publication Data

US 2017/0237570 A1    Aug. 17, 2017

(51) Int. Cl.
*H04L 9/32* (2006.01)
*H04L 29/06* (2006.01)

(52) U.S. Cl.
CPC ........ *H04L 63/0442* (2013.01); *H04L 9/3236* (2013.01); *H04L 9/3247* (2013.01); *H04L 63/123* (2013.01); *H04L 63/0823* (2013.01); *H04L 2209/38* (2013.01); *H04L 2209/56* (2013.01)

(58) Field of Classification Search
CPC ..... H04L 9/3247; H04L 63/0435; H04L 9/08; H04L 63/061; H04L 9/0844; H04L 63/0428; H04W 12/04
See application file for complete search history.

(56) References Cited

U.S. PATENT DOCUMENTS

| 5,655,075 | A | * | 8/1997 | Saito | H04L 29/06 714/48 |
| 5,682,527 | A | * | 10/1997 | Cooper | G06F 11/1471 |
| 7,304,996 | B1 | * | 12/2007 | Swenson | H04L 45/7453 370/229 |
| 7,983,421 | B2 | * | 7/2011 | Chandrasekaran | H04L 9/0891 380/277 |

(Continued)

OTHER PUBLICATIONS

Satoshi Nakamoto, "Bitcoin: A Peer-to-Peer Electronic Cash System", first published on the internet in Nov. 2008.

(Continued)

*Primary Examiner* — Catherine B Thiaw
*Assistant Examiner* — Sanchit K Sarker
(74) *Attorney, Agent, or Firm* — Fox Rothschild LLP

(57) ABSTRACT

Methods and systems for providing secure recording of revisions made to electronic documents, using secure methods to validate the recorded changes, are disclosed. An electronic device making a change to an electronic document can transmit the change to the network. An audit log chain is residing on the network and shared among all the nodes on the network. A node on the network can verify a change of document made by other nodes and add a new block to the chain using one-way hashes, making the chain resistant to tampering. If an invalid block is detected, the system can send an auditing alert to the network. The audit log can be strongly resistant to tampering, providing reliable evidence for use in audit compliance, investigations, and business or court record keeping.

23 Claims, 5 Drawing Sheets

(56) References Cited

U.S. PATENT DOCUMENTS

| | | | |
|---|---|---|---|
| 8,078,956 B1* | 12/2011 | Feldman | G06F 17/2247 715/223 |
| 8,321,382 B2 | 11/2012 | Vandervort et al. | |
| 8,533,582 B2 | 9/2013 | Rao et al. | |
| 9,065,842 B2 | 6/2015 | Vandervort | |
| 9,442,806 B1* | 9/2016 | Bardale | G06F 11/1453 |
| 2005/0027702 A1* | 2/2005 | Jensen | G06F 17/30882 |
| 2005/0122965 A1* | 6/2005 | Heinla | G06O 20/102 370/357 |
| 2010/0169967 A1* | 7/2010 | Khosravi | G06F 21/52 726/22 |
| 2012/0096536 A1* | 4/2012 | Dewey | H04L 63/123 726/11 |
| 2013/0031067 A1* | 1/2013 | Iyer | G06F 11/302 707/703 |
| 2014/0279843 A1* | 9/2014 | Von Weihe | G06F 17/2288 707/608 |
| 2014/0344267 A1* | 11/2014 | LeBert | G06F 17/30893 707/736 |
| 2015/0012550 A1 | 1/2015 | Thirugnanasundaram et al. | |
| 2015/0032687 A1* | 1/2015 | vanderZweep | G06F 17/30289 707/609 |
| 2016/0004986 A1* | 1/2016 | Pothukuchi | G06Q 10/08 705/7.25 |
| 2016/0007142 A1* | 1/2016 | Anderson | H04W 76/10 455/41.1 |
| 2017/0054740 A1* | 2/2017 | Mitchell | H04L 51/18 |
| 2017/0083860 A1* | 3/2017 | Sriram | H04L 63/126 |
| 2017/0237569 A1* | 8/2017 | Vandervort | H04L 9/3247 713/171 |
| 2017/0237570 A1* | 8/2017 | Vandervort | H04L 63/0442 713/176 |
| 2017/0250972 A1* | 8/2017 | Ronda | H04L 9/08 |

OTHER PUBLICATIONS

Block Chain, Bitcoin Wiki, printed from the internet Feb. 8, 2016, https://en.bitcoin.it/wiki/Block_chain.

* cited by examiner

```
-{ "name": "Roy Jones", "contacts":[]}
+{ "name": "Roy Jones", "contacts" :[{ "created_at": "2015-07-01-01:05:45 UTC", "updated_at": "2015-07-01: 01:05:45 UTC", "reason": "Presents with high fever, generalized achy muscles, vomiting and fatigue", "diagnosis": "testing for the flu"}]}
```

FIG. 4

METHOD AND SYSTEM FOR SERVER BASED SECURE AUDITING FOR REVISIONING OF ELECTRONIC DOCUMENT FILES

BACKGROUND

This patent document relates to versioning control in an electronic document file management system. More specifically, the present disclosure relates to a secure revisioning audit system for electronic document files.

Electronic document files, which may include documents, programming files and data records change over time. They go through revisions, additions and deletions. Tracking these changes, so any previous version of a document can be recreated, is called version control or source control, and it is well known in computer programming and document management systems. When a new version of any source is created, the difference (called a diff) between the new version and the old version is created. Any version can be recreated by combining all diffs up to that version, or subtracting diffs from the latest version. The repositories of these diffs are invaluable tools for programmers, however, they are not intended to be secure. Some version control systems make it fairly easy to edit entries in the revision system. This may not be of a concern for most documents because it is enough to be able to access the most recent version, whereas older versions are simply obsolete. However, for some high stakes electronic documents, such as electronic medical records (or electronic health records, sometimes referred to as EHRs), bank records or the documentation of a criminal investigation, it is important not only to have the most recent version but to be able to audit the changes made and who made them.

There can be many applications to drive the need for an audit trail. For example, medical records may be reviewed to determine how treatment mistakes are made, either for educational purposes or as part of a lawsuit. Financial records might be audited for compliance to laws and regulations or to discover embezzling or other misconduct. Criminal investigative records, including such disparate items as interview notes, crime scene photos and DNA test results, are so critical evidence in a court that any alternation can have significant consequences.

While creating an audit trail is relatively easy, protecting it from tampering or simple error is difficult. Those who would alter or destroy these records are normally highly motivated and may only need a little knowledge of database hacking or someone else's passwords to achieve their goal.

In a related field, Bitcoin technology, which is developed for electronic commerce, includes elements that can greatly improve the process of keeping records in an auditable and secure form. The heart of this technology is a data structure called the blockchain. In essence, a blockchain is a data structure that links successive transaction records with one-way cryptographic hashes. Coupled with a processor intensive process called "Proof of Work" and a distributed consensus system, data written to a blockchain is extremely resistant to changes of any kind.

While Bitcoin technology is developed for securing transactions for electronic commerce that involves money (digital or otherwise), it would not work for securing and auditing records with no money changing hands in a transaction. For example, the Bitcoin protocol uses randomly generated addresses to make transactions anonymous. This portion of the protocol is incompatible with the goals of verifiable auditing, as the identity of the sender (the person currently editing a document) is tied to the person responsible for making the change of the document and should not be anonymous. Further, the Bitcoin protocol specifies all details (except for 40 bytes of arbitrary data) of the data included in a transaction. It is not adaptable to the type of diff data in document versioning control. A way of keeping records that is reliable and resistant to tampering is therefore needed.

This document describes devices and methods that are intended to address issues discussed above and/or other issues.

SUMMARY

Embodiments for server based secure revisioning auditing for electronic document files are disclosed. In one embodiment, a system for securely auditing revisions to an electronic document may include a processing device and a hardware-based non-transitory storage medium containing program instructions that will receive a signed data packet, which includes an identifier for a user and a diff representing a difference between a first version of an electronic document and a revision of the electronic document. The system may group multiple signed data packets into a block, access a chain on a communication network, and validate the block. If validation of the block succeeds, the system may update the chain based on the created block so that the chain is available to a plurality of authorized additional user electronic devices via the communication network. If validation of the block fails, the system may generate an alert and transmit the alert to the communication network.

In one embodiment, the system may also verify a signed data packet before grouping it into a block. In verifying a signed data packet, the system may verify the signed data packet against one or more rules to determine whether the one or more rules are satisfied. In one embodiment, if at least one of the one or more rules is not satisfied, the system may generate an alert and transmit it to the communication network. Alternatively and/or additionally, the system may verify if the block is already validated by another node on the communication network, and if so, the system may choose to abandon the validation of the block and move to the next. In one embodiment, the system may obtain an updated chain of the communication network if the system is offline for a period of time. In another embodiment, the system may obtain an updated chain of the communication network if one or more quality criteria associated with validating the block are not satisfied.

BRIEF DESCRIPTION OF THE DRAWINGS

FIG. 4 depicts an example of a diff record.

DETAILED DESCRIPTION

Figure 1:
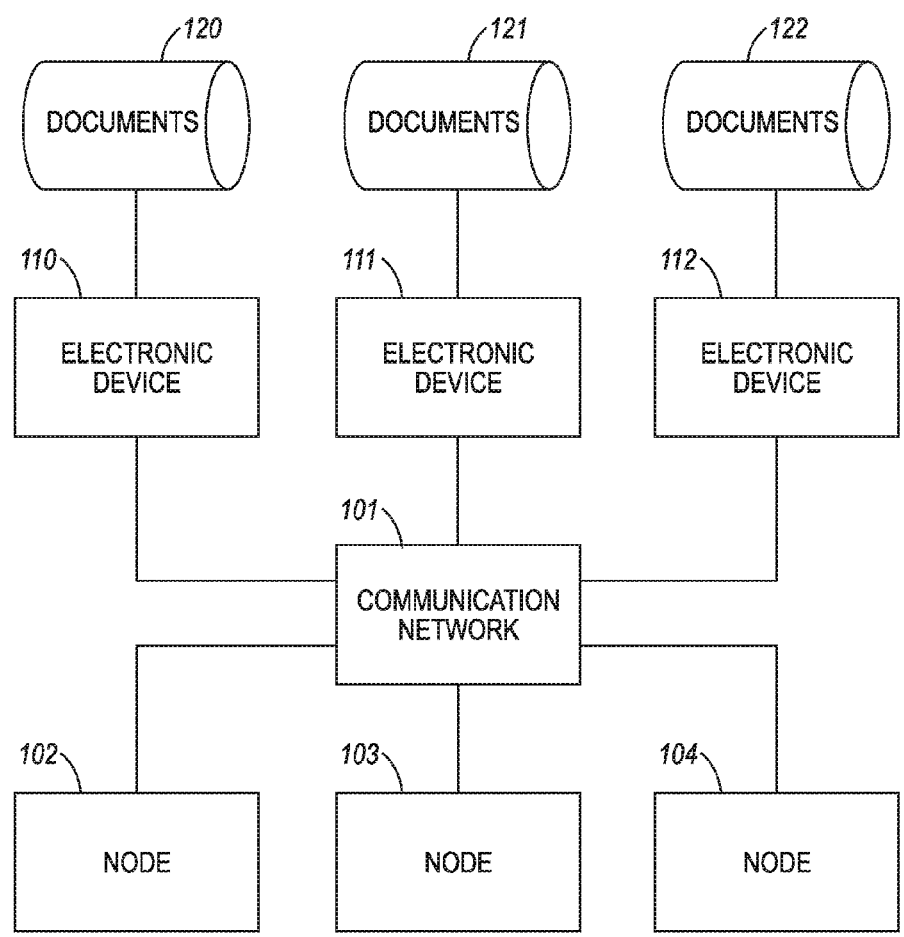
FIG. 1 depicts an example of the auditing system according to one embodiment.

This disclosure is not limited to the particular systems, methodologies or protocols described, as these may vary. The terminology used in this description is for the purpose of describing the particular versions or embodiments only, and is not intended to limit the scope.

As used in this document, any word in singular form, along with the singular forms "a," "an" and "the," include the plural reference unless the context clearly dictates otherwise. Unless defined otherwise, all technical and scientific terms used herein have the same meanings as commonly understood by one of ordinary skill in the art. All publications mentioned in this document are incorporated by reference. Nothing in this document is to be construed as an admission that the embodiments described in this document are not entitled to antedate such disclosure by virtue of prior invention. As used herein, the term "comprising" means "including, but not limited to."

In this document, the term "electronic device" refers to a device having a processor and a non-transitory, computer-readable medium (i.e., memory). The memory may contain programming instructions in the form of a software application that, when executed by the processor, causes the device to perform one or more processing operations according to the programming instructions. An electronic device also may include additional components such as a touch-sensitive display device that serves as a user interface, as well as a camera or other image capturing device. An electronic device also may include one or more communication hardware components such as a transmitter to enable the device to send signals to other devices or a receiver to receive signals from other devices, whether via a communications network or via near-field or short-range communication protocols. Examples of electronic devices include computer servers, personal computers, multi-function devices, smartphones, tablet computing devices, electronic readers, and the like.

The term "electronic document" refers to any piece of information stored electronically, be it text, image, video or a hybrid of those. It may be a simple electronic file or a data structure that is stored in a storage medium or a memory of a processing device.

The term "diff" refers to a quantifiable measure or assessment of the difference between a first version of an electronic document and a revision of the electronic document. In one embodiment, it may be in a similar data structure as the result of UNIX "diff" command. In another embodiment, it may be a proprietary or standard data structure to represent a difference between two versions of a document. For example, the diff for a text document may be represented by ASCII characters, whereas the diff for an image document may be represented by binary data. A diff can result from comparing the contents of a current document from its immediate preceding version, or comparing the contents of a current document from older version several changes removed up to the original version.

The term "record" refers to a data structure representing an instance of a diff. It may be protected by a cryptographic scheme using a private/public key pair.

The term "transaction" refers to a change to an electronic document that results in the generation of a diff.

The term "block" refers to a list of transactions in a data structure.

Each of the terms "blockchain" and "chain" refers to a data structure containing a chain of blocks.

Each of the terms "server" or "node" refers to a computing device having a processor, either locally or on a network, which functions to verify the legitimacy of a transaction initiated by a different electronic device. The terms "first," "second" and the like do not limit to any particular element, any particular order, or the number of elements. They are used to purely describe distinct elements and provide antecedent basis thereof.

With reference to FIG. 1, an overall auditing system is shown according to an embodiment. The system includes a communication network 101, one or more servers (nodes) 102, 103, 104, and one or more electronic devices 110, 111, 112 on the communication network. Each of the electronic devices may create and edit the electronic documents 120, 121, 122 and may have a capability to verify identity of those who use the document and securely send every change to every record to the auditing system via the communication network 101. In one embodiment, each of the nodes on the communication network can be installed in each of the organizational units in the overall system, such as the hospital, the critical care unit or the doctor's office. The node in each of these organizational units can create its own records in the blockchain or verify the records created by other nodes. In one embodiment, the auditing system uses an encryption process, such as public key cryptography, to sign all record changes in an electronic document (with the private half of a key pair) and to verify that records have not been altered (with the public half of the key pair). This is important in ensuring the security of record changes before they are fixed in the blockchain. The security of the disclosed system and method may improve as the system becomes larger. Therefore, it is very appropriate for large enterprises such as regional hospital systems or multi-national corporations.

The details of a transaction lifecycle in the disclosed system will be further explained. Before a transaction can begin, a user must be identified by the system. The authentication can be implemented using any known methods in the field. Typically in modern systems authentication is done by typing in a username and password. Stronger methods, such as two-factor identification with biometric features, such as fingerprints, are also available.

In one embodiment, a suitably authenticated and authorized user is given access to a document. In most modern systems, electronic documents having the highest stakes are accessed through customized software that presents form fields to be filled in and stores the resulting documents in a database. For purposes of this disclosure, these database records work as a more traditional document (e.g., a file generated by a word processing application such as Microsoft Word). In one example according to one embodiment, the user will make some changes. For example, accountants may enter a transaction code, doctors may order a test, managers may enter a note in a personnel record, auditors may note an error. In one embodiment, the user may cause a document processing application to store the changes to a memory as an updated electronic document. In another embodiment, the system may automatically save the changes as they are being made by the user.

Figure 2:
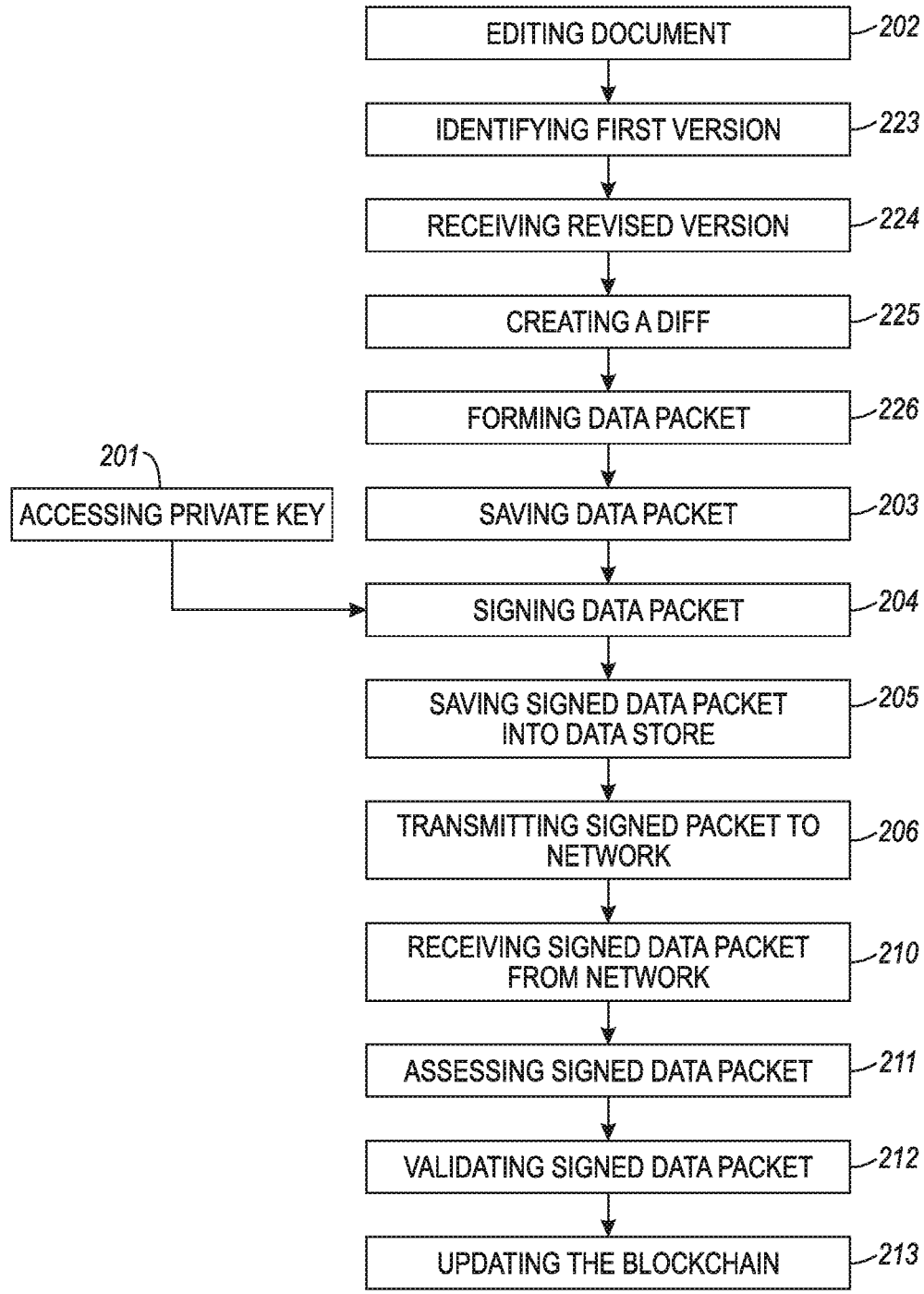
FIG. 2 depicts a flow chart of a portion of a revision auditing process according to one embodiment.

As shown in FIG. 2, according to one embodiment, a user works on an electronic device or a terminal, which accesses or generates a private key for the user 201. Keys can be issued by the electronic device the user is using, by a backend store (e.g. on a remote server) or a hard wallet (from a USB drive or other communicatively connected memory device). Each key is associated with one and only one user of the system, i.e., each key is unique to the user. However, the disclosed system does not restrict users to one public private key pair at a time. For example, one user may have many key pairs, even going as far as having a new pair for every transaction. Keys can be generated by any existing methods in the field. For example, with Bitcoin, keys are managed by a piece of software called a wallet. It is possible for users to carry wallet software on a portable memory device such as a USB thumb drive (i.e., a hard wallet). There are also deterministic methods for creating keys from a seed such as a password or biometric identifier.

In one embodiment, once a user has made a change to an electronic document 202, the system generates and saves a data packet 203. In one embodiment, the system identifies a first version of the document 223, receives a revised version 224, analyzes the first version and the revised version to create a diff 225 between the first version and the revised version. The system may form a data packet 226 that encapsulates the changes made to the document (diff) and the identifier for the user who has made the changes. Additionally, the system may also add additional metadata to the data packet, such as an identifier for the electronic device or location at which the user has made the changes. In another embodiment, a timestamp can also be added. In a non-limiting example, a sample diff of a simulated medical record is shown in FIG. 4. In this example, both the original version and the altered version are converted as JSON (Java Script Object Notation) documents, then the standard Unix diff generation code is used to produce the diff. Other methods, such as converting to XML first, or comparing records byte by byte are also possible. Additionally and/or alternatively, the system can also encrypt the data in the diff using any now or hereafter known encryption technologies in the field, to increase the level of security. In another embodiment, the diff is not limited to text but can also be used for images in a document, in which the diff can represent incremental changes between old and new images or represent the complete new image without comparing to the old image.

With further reference to FIG. 2, the system may access a user's private key 201 and sign off the data packet by the user's private key 204. The system may save the signed data packet into a data store as part of a transaction 205 and transmit it to a node on a network such as the Internet 206 and/or another communication network. A blockchain that includes the transaction will be cooperatively developed by multiple nodes on the network. In one embodiment, when one node receives a transaction from an electronic device, it passes the transaction on to other nodes it has communicated with. In this way, even a very large number of nodes may all be informed of new transactions in a fraction of time, such as under a few seconds.

In one embodiment, nodes must be validated as legitimate members of the network because of the high security nature of the auditing system. The documents whose changes are stored on the blockchain are not public documents, therefore, the computers that handle them may be under the control of a single organization, be it a hospital, government department or international business. Likewise, all transactions and finalized blocks will only be accepted if they come from known sources. This is to prevent network intrusions that might seek to insert a hostile system into the network. The system will only allow legitimate members (nodes) on the network to download and view a transaction or the blockchain. In another embodiment, the system will also give nodes full read-write access to update the blockchain.

A legitimate node may receive a signed transaction data packet from the network 210 and access the contents of the transaction 211. The node may validate the signed data packet 212, and upon validation of the signed data packet, update the blockchain 213. In some embodiments, a node may be permitted to update a blockchain with a new transaction only if at least a threshold number (e.g., a majority) of the nodes on the network have verified the blockchain.

Figure 3:
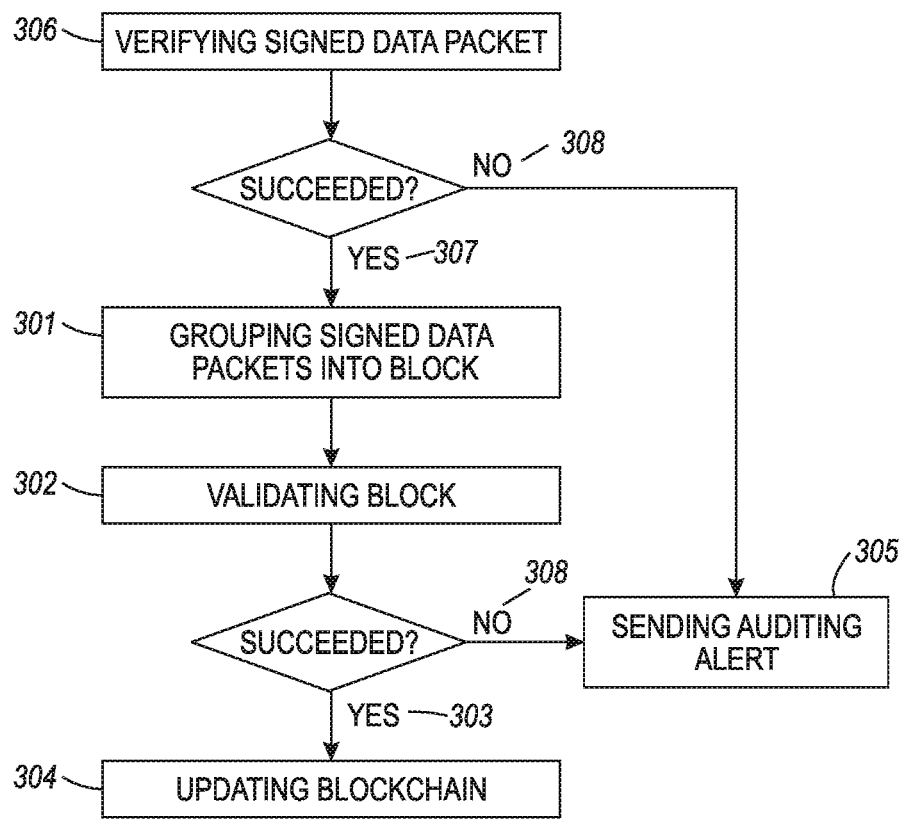
FIG. 3 depicts a flow chart of another portion of a revision auditing process according to one embodiment.

With reference to FIG. 3, in validating the signed data packet, at least some of the nodes may verify the contents of the signed transaction data packet 306, upon successful verification of the signed transaction data packet 307, group available transaction data packets into blocks 301, and then validate a block 302 by, for example, creating what is known as a proof of work on the block. A proof of work is a piece of data or process that can be used to verify the contents of a blockchain. If the node has successfully created a proof of work, the block is valid 303 and the node may update the blockchain with the new block 304. If the node fails to verify a signed transaction data packet or fails to create a proof of work 308, it may send an auditing alert 305.

In verifying a transaction data packet 306, a node also may check the transaction against various rules. The rules can be kept on centralized servers, while in more distributed systems, all nodes would have a copy of all rules. In one embodiment, a node may determine whether a legitimate change (diff) has been made based on a timestamp of each transaction. For example, a node may compare the timestamp of a doctor's transcript with the office hours of the doctor's office. If the timestamp of the doctor's transcript is outside of the doctor's office hours, the system may determine that the change (diff) is not legitimate and subsequently send an alert. In another embodiment, the node may check whether a document change made by a doctor against the doctor's access rights to the document and determine whether the doctor has changed what he or she is allowed to change. In other embodiments, the rules may include security rules, i.e. users and their roles allowed to perform certain actions. The rules may also include business rules, i.e., how actions must be grouped, for example, when a credit is given to a customer, the system may require a complementary product be scheduled for shipment as well.

When one or more rules are not satisfied, the system may reject a transaction. An example alert would include the transaction hash, and the reason for rejecting it (i.e. what rule was violated). In one embodiment, the system may flag a rejected transaction with the appropriate rule and written to the blockchain like any other transaction. This would enable strong auditing. In another embodiment, the system may drop a rejected transaction and send a notification to the electronic device that generated them to revert the document to a version or form that existed before the offending change. In another embodiment, if the failure of verification is related to a corrupted data structure, the system may simply request the sender to re-send. While the system may support the verification of transactions, in one embodiment, this method can also be optional, and the system may proceed to group transactions into blocks 301 and validate blocks (creating a proof of work) 302, which will be described in detail as below.

In grouping transactions into blocks 301, the node may choose the size data for grouping (which can vary greatly among diffs) and target at a defined size, such as 500 MB of data per block. In another embodiment, the node may group by raw number, i.e., at first come, first served basis until the size of the block reaches a threshold such as 500 MB. In another embodiment, the node could prioritize certain documents or types of changes or even people making changes being added to a block first.

In validating a block 302, the node may create a proof of work for the block using any of various methods. In one embodiment, the node may add a nonce (a random number)

to the block data, then hash the block data. If the hash fails to meet the needs of the proof of work, the nonce is changed and a new hash is made. Because of the nature of hashing, the new hash will be completely different form the old one. This process may be repeated until the resulting hash passes the test.

An example test for a proof of work may convert the generated hash value into a number in binary format (1's and 0's) and compare that number to a target value. If the number is less than the target value, the proof of work passes the test. If it is greater than that target number the proof of work would fail. The target number of the proof of work may be changed in order to accommodate an increased number of nodes on the network (thus making it harder to find a good number reduces the number of "collisions" with several nodes creating a good block simultaneously) or reduced when to deal with a large amount of data traffic (allowing the system to generate more blocks in a shorter time when there is a need). Alternate methods of proof of work include more complex mathematical operations, such as generating a valid series of prime numbers. Various embodiments include methods of proof of work that have been developed to date, and that may be developed in the future.

When creating the proof of work, one node may make the nonce, the data block and the hash all available to the other nodes on the network, which can reproduce the hash and test it for meeting requirements in almost no time. If a proof of work is not successfully created, this may indicate that a tampering on the signed diff data packet may have occurred, or an invalid changes or a ill formed packets (e.g. caused by bad hardware that corrupts data traffic) may exist. The system may send an auditing alert 305 in a similar method as when the node fails to verify a transaction. If a proof of work is successfully created, the node may accept a valid block by expanding the blockchain using the hash of the accepted block as the previous hash.

In one embodiment, the list of transactions (hash) can be built using the Merkle tree of all transactions in the block. Other linking methods can be used as well. A node can run as a full network node, i.e., a node that can create a block from many transactions. There are also nodes that just relay information from other nodes on the network and compare hashes to ensure new blocks are valid. For example, a node may only obtain the longest blockchain from the network and keep a copy of block headers of the longest chain. In some embodiments, these nodes could also prioritize and route transactions.

In one embodiment, there is only one blockchain on the network that is accessible to all other nodes. In another embodiment, a node may choose to obtain an updated chain from the communication network if the node is off-line for a period of time. Alternatively and additionally, the system may perform quality check to determine whether one or more quality criteria associated with creating and/or validating a block are satisfied. If one or more quality criteria are not satisfied, the system may determine to obtain an updated chain. For example, if a node finds it has generated bad blocks many times in a row, it could simply decide to dump its own copy of the blockchain and use the most current chain on the network. In another embodiment, a node's blockchain may be out of sync with the rest of the network for many reasons, such as network issues, bad software updates and corrupted database files. In that case, the node would have to refresh some or all of the blocks in its copy of the blockchain from another source. In one embodiment, while the node refreshes one or more blocks from another source, it verifies the integrity of hashes of these blocks.

When a node has successfully created a proof of work for a valid block, it sends the solution (the proof of work) to the other nodes. In one embodiment, when a node receives a valid block (the proof of work is valid) from other nodes, it will abandon any other block that it has been building (which includes many of the same transactions) and begin working on the next.

In one embodiment, at intervals, a node may insert a transaction about its own state into the blockchain in the same way other transactions are inserted, and transmit the updated blockchain to other nodes. This transaction describes various operational information such as system name, uptime, number of blocks processed, number of transactions in the unassigned pool, current time and location and any other relevant data. This transaction entry serves various purposes, such as: (1) it provides a quality check, showing that a node is operating correctly; and b) it shows when a new node is added to the network. This helps catch rogue nodes (because only known nodes may participate in transaction and block creation as explained above). This transaction also provides an audit check on processed blocks. That is, since the number of nodes is known, the rate at which they produce their data should be predictable. Any sudden increases or decreases in the rate indicate problems such as network issues or even tampering with nodes.

The use of the blockchain, as disclosed above, is auditable. The more blocks there are beyond a given point of interest, the more difficult it is for anyone to make changes at that point. In other words, in re-constructing a document from the diff, the system may determine that blocks at certain length from a given point of interest are correct and of very high confidence. In general, the newest blocks are those that are the least secure and the oldest the most secure.

In one embodiment, the disclosed blockchain-based auditing system may work in parallel with any database system and it may offer various advantages such as achieving high security. For example, ordinary databases can be hacked, logins can be stolen but a blockchain based system will show quickly when inconsistencies in the record appear.

As can be appreciated to one ordinarily skilled in the art, the above disclosed system and method can be advantageous in many applications since it provides a cryptographically secured record of all changes to important records, so that accuracy can be guaranteed and attempts to subvert that accuracy traced. For example, hospitals, banks, government agencies and even the companies that make software for airplanes and nuclear power plants, can benefit from having not just an audit trail but an incorruptible record of all changes. These benefits allow record owners to recover work that may have been altered or destroyed from more traditional control systems and pinpoint the exact moment when things went wrong.

Figure 5:
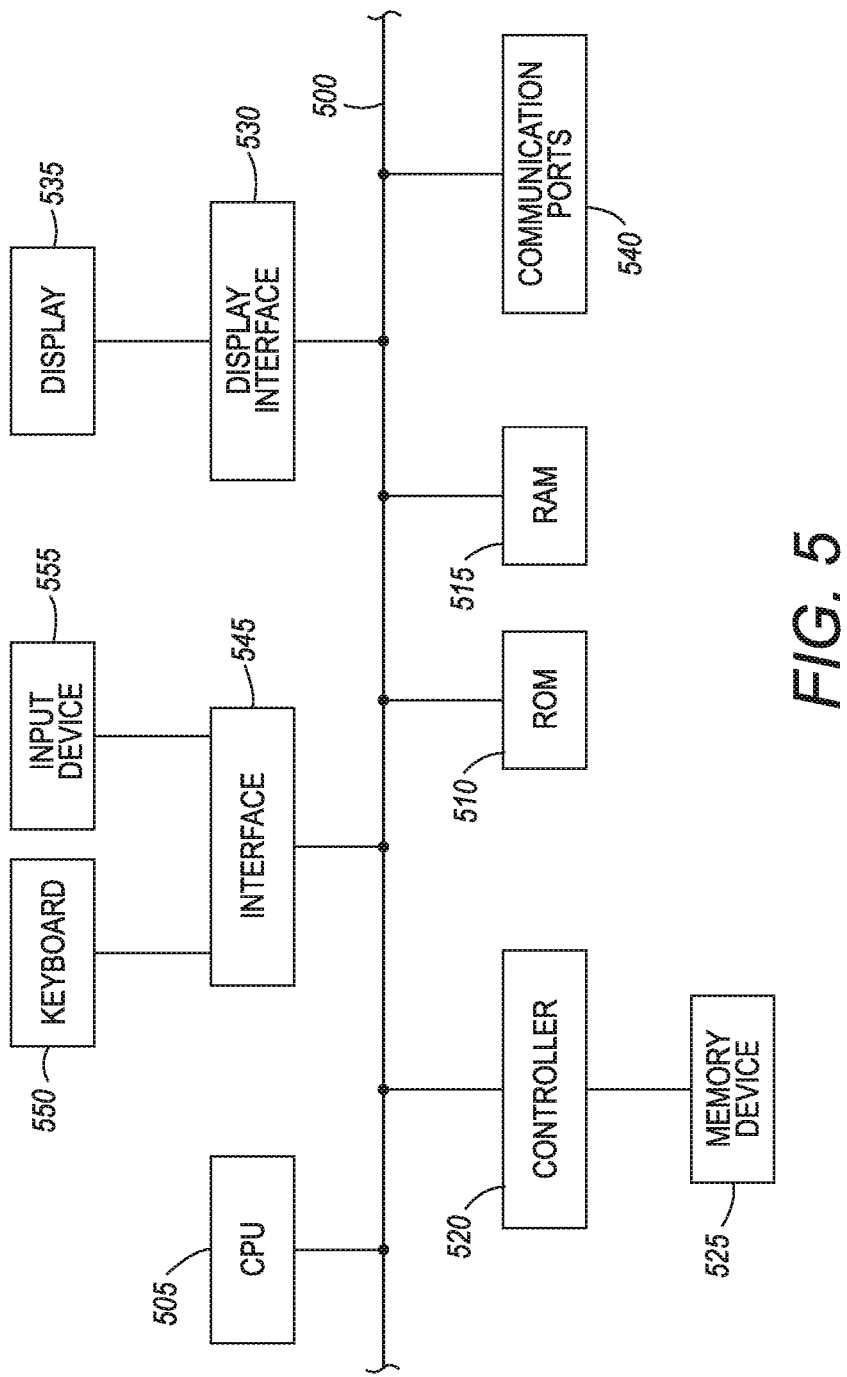
FIG. 5 depicts various embodiments of one or more electronic devices for implementing the various methods and processes described herein.

FIG. 5 depicts an example of internal hardware that may be included in any of the electronic components of the system, the user terminal, node or server or another device in the system. An electrical bus 500 serves as an information highway interconnecting the other illustrated components of the hardware. Processor 505 is a central processing device of the system, configured to perform calculations and logic operations required to execute programming instructions. As used in this document and in the claims, the terms "processor" and "processing device" may refer to a single processor or any number of processors in a set of processors. Read only memory (ROM), random access memory (RAM), flash memory, hard drives and other devices capable of storing electronic data constitute examples of memory devices 510. A memory device may include a single device or a collection of devices across which data and/or instructions and/or one or more other electronic documents are stored.

In one embodiment, the system may contain program instructions on a non-transitory storage medium that can be executed on the processing device or an ASIC (Application Specific Integrated Circuits) to be able to handle computation intensive calculations. Alternatively and/or additionally, because creating a proof of work is so processor intensive, the program instructions may also be executed on a GPU (Graphics Processing Unit).

An optional display interface 530 may permit information from the bus 500 to be displayed on a display device 545 in visual, graphic or alphanumeric format. An audio interface and audio output (such as a speaker) also may be provided. Communication with external devices may occur using various communication devices 540 such as a transmitter and/or receiver, antenna, an RFID tag and/or short-range or near-field communication circuitry. A communication device 540 may be attached to a communications network, such as the Internet, a local area network or a cellular telephone data network.

The hardware may also include a user interface sensor 545 that allows for receipt of data from input devices 550 such as a keyboard, a mouse, a joystick, a touchscreen, a remote control, a pointing device, a video input device and/or an audio input device. Data also may be received from other controllers 520 and memory device 525 such as a USB flash drive. A positional sensor 555 may be included to detect the location of the user, and such information can be included in the signed data packet for verification.

The above-disclosed features and functions, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

The invention claimed is:

1. A system for securely auditing revisions to an electronic document, the system comprising:
   a processing device; and
   a hardware-based non-transitory storage medium operably connected to the processing device and configured to store a set of instructions that, when executed, cause the processing device to:
      receive a signed data packet, wherein the signed data packet comprises:
         a diff data structure that represents a difference between a first version of an electronic document and a revision of the electronic document, and
         an identifier associated with a user who created the revision,
         wherein the signed data packet is signed with a private key associated with the user,
      create a block by grouping the signed data packet and a plurality of additional signed data packets, wherein at least one of the additional signed data packets comprises:
         a second diff data structure representing either a second difference between two versions of the electronic document or a difference between two versions of a second electronic document, and
         a second identifier associated with a user responsible for the second difference or the difference between two versions of the second electronic document,
      access a blockchain on a communication network,
      validate the block,
      if validation of the block succeeds, update the blockchain to include the block so that the blockchain is available to a plurality of authorized additional user electronic devices via the communication network, and
      if validation of the block fails, generate an alert and transmit the alert to the communication network.

2. The system of claim 1, wherein the instructions further comprise additional instructions that, when executed, cause the processing device to:
   verify the signed data packet before creating the block; and
   upon verification of the signed data packet, create the block.

3. The system of claim 2, wherein the instructions for causing the processing device to verify the signed data packet comprise additional instructions that, when executed, cause the processing device to:
   verify the signed data packet against one or more rules to determine whether the one or more rules are satisfied; and
   generate an alert when at least one of the one or more rules is not satisfied.

4. The system of claim 1, wherein the instructions for causing the processing device to validate the block further comprise instructions that will cause the processing device to:
   verify if the block is already validated by an additional node of the system; and
   abandon the validation of the block if the block is already validated.

5. The system of claim 1, wherein the set of instructions further comprises instructions that will cause the processing device to obtain an updated blockchain if the processing device is offline for a period of time.

6. The system of claim 1, wherein the set of instructions further comprises instructions that will cause the processing device to obtain an updated blockchain if one or more quality criteria associated with validating the block are not satisfied.

7. The system of claim 1, wherein the signed data packet further comprises at least one of a system name, an uptime, a number of transactions processed, a number of transactions in an unassigned pool, a current time and location of an electronic device that includes the processing device, or a user of the electronic device that includes the processing device.

8. The system of claim 1, wherein the set of instructions comprises further instructions that will cause the processing device to respond to a request for validation of the processing device.

9. The system of claim 1, wherein the processing device is a component of a remote server on the communication network.

10. A method for securely auditing revisions to an electronic document, the method comprising:
   receiving, by a processing device, a signed data packet, wherein the signed data packet comprises a diff data structure representing a difference between a first version of an electronic document and a revision of the electronic document, and an identifier associated with a user who created the revision, wherein the signed data packet is signed with a private key associated with the user;

creating, by the processing device, a block by grouping the signed data packet and a plurality of additional signed data packets, wherein at least one of the additional signed data packet comprises:
- a second diff data structure representing either a second difference between two versions of the electronic document or a difference between two versions of a second electronic document, and
- a second identifier associated with a user responsible for the second difference or the difference between two versions of the second electronic document;

accessing a blockchain on a communication network;
validating the block;
if validation of the block succeeds, updating the blockchain to include the block so that the blockchain is available to a plurality of authorized additional user electronic devices via the communication network; and
if validation of the block fails, generating an alert and transmit the alert to the communication network.

11. The method of claim 10, further comprising:
verifying, by the processing device, the signed data packet before creating the block; and
upon verification of the signed data packet, creating the block.

12. The method of claim 11, wherein verifying the signed data packet comprises:
verifying the signed data packet against one or more rules to determine whether the one or more rules are satisfied; and
generating an alert when at least one of the one or more rules is not satisfied.

13. The method of claim 10, wherein validating the block comprises:
verifying if the block is already validated by an additional node of the system; and
abandoning the validation of the block if the block is already validated.

14. The method of claim 10, further comprising obtaining an updated blockchain if the processing device is offline for a period of time.

15. The method of claim 10, further comprising obtaining an updated blockchain if one or more quality criteria associated with validating the block are not satisfied.

16. The method of claim 10, wherein the signed data packet further comprises at least one of a system name, an uptime, a number of transactions processed, a number of transactions in an unassigned pool, a current time and location of a user electronic device that includes the processing device, or a user of the electronic device that includes the processing device.

17. The method of claim 10, further comprising responding to a request for validation of the processing device.

18. The method of claim 10, wherein the processing device is a remote server on the communication network.

19. A system for securely auditing revisions to an electronic document, the system comprising:
a processing device; and
a hardware-based non-transitory storage medium operably connected to the processing device and configured to store a set of instructions that, when executed, cause the processing device to:
  receive a signed data packet, wherein the signed data packet comprises:
    a diff data structure representing a difference between a first version of an electronic document and a revision of the electronic document, and
    an identifier associated with a user who created the revision,
    wherein the signed data packet is signed with a private key associated with the user,
  verify the signed data packet, and
  upon verification of the signed data packet,
    create a block by grouping the signed data packet and a plurality of additional signed data packets, wherein at least one of the additional signed data packets comprises:
      a second diff data structure representing either a second difference between two versions of the electronic document or a difference between two versions of a second electronic document, and
      a second identifier associated with a user responsible for the second difference or the difference between two versions of the second electronic document,
    access a blockchain on a communication network,
    validate the block,
    if validation of the block succeeds, update the blockchain to include the block so that the blockchain is available to a plurality of authorized additional user electronic devices via the communication network, and
    if validation of the block fails, generate an alert and transmit the alert to the communication network.

20. The system of claim 19, wherein the instructions for causing the processing device to verify the signed data packet comprises additional instructions that, when executed, cause the processing device to:
verify the signed data packet against one or more rules to determine whether the one or more rules are satisfied; and
generating an alert when at least one of the one or more rules is not satisfied.

21. The system of claim 19, wherein the instructions for causing the processing device to validate the block further comprising instructions that will cause the processing device to:
verify if the block is already validated by an additional node of the system; and
abandon the validation of the block if the block is already validated.

22. The system of claim 19, wherein the set of instructions further comprises instructions that will cause the processing device to obtain an updated chain if the processing device is offline for a period of time.

23. The system of claim 19, wherein the set of instructions further comprises instructions that will cause the processing device to obtain an updated chain if one or more quality criteria associated with validating the block are not satisfied.

* * * * *